US00PP19763P2

(12) United States Plant Patent
Ballington

(10) Patent No.: US PP19,763 P2
(45) Date of Patent: Feb. 24, 2009

(54) STRAWBERRY PLANT NAMED 'GALLETTA'

(50) Latin Name: *Fragaria×ananassa*
Varietal Denomination: Galletta

(75) Inventor: James R. Ballington, Cary, NC (US)

(73) Assignee: North Carolina Agriculture Research Service, Raleigh, NC (US)

( * ) Notice: Subject to any disclaimer, the term of this patent is extended or adjusted under 35 U.S.C. 154(b) by 1 day.

(21) Appl. No.: 12/011,046

(22) Filed: Jan. 24, 2008

(51) Int. Cl.
*A01H 5/00* (2006.01)

(52) U.S. Cl. ..... Plt./208
(58) Field of Classification Search ..... Plt./208
See application file for complete search history.

*Primary Examiner*—Annette H Para

(57) ABSTRACT

*Fragaria×ananassa* Duchense 'Galletta' is a new and distinct variety of strawberry plant that has the following unique combination of desirable features that are outstanding in a new variety.

1. Early ripening and large fruit size.
2. Yields equal to standard cultivars that are main season ripening.
3. Very attractive symmetrical fruit with deep red skin color and medium red flesh.
4. Good fruit quality, flesh firmness and skin toughness.
5. Broad plant adaptation in the southeastern US.

2 Drawing Sheets

Latin name of the genus and species:

The Latin name of the novel strawberry variety disclosed herein is *Fragaria×ananassa* Duchense.

Variety denomination:

The inventive cultivar of *Fragaria×ananassa* disclosed herein has been given the variety denomination 'Galletta'.

BACKGROUND OF THE INVENTION

The present invention relates to a new and distinct cultivar of *Fragaria×ananassa* Duchense (strawberry) grown as a fruiting herbaceous perennial for commercial agriculture. Strawberries are typically consumed both fresh and in a number of processed products.

The new and distinct variety of strawberry (*Fragaria×ananassa* Duchense) originated from the hand pollinated cross of NCH 87-22 (unpatented)×Earliglow (unpatented) made in Beltsville, Md., in 1991.

Seeds from this hand pollination were germinated in winter 1991/1992 and the resulting seedlings established at Salisbury, N.C., in spring 1992. When the seedlings fruited in spring 1993, an elite genotype designated NCS 93-05 was selected for its early ripening large size attractive high quality fruit by James R. Ballington. Runner plants of the original plant of NCS 93-05 were rooted in plug trays under intermittent mist in Raleigh, N.C., following the 1993 fruiting season, and then transplanted to a field nursery at Salisbury, N.C., for production of additional plants. In summer, 1994, runner plants from the plants established in the field nursery were rooted in plug trays under intermittent mist in Raleigh, N.C., and then transplanted into duplicate annual hill culture (plasticulture) plot trials at Castle Hayne, Reidsville and Fletcher, N.C., in late summer for evaluation of fruit in spring 1995. These trials were also established at the three locations in late summer 1995 and 1996 for evaluation in 1996 and 1997 respectively. Based on its performance in these initial trials, NCS 93-05 was propagated again from runner plants in plug trays under intermittent mist in Raleigh, N.C., and established in a replicated annual hill culture trial at Fletcher, N.C., in late summer 1998, for evaluation in spring 1999, and Charleston, S.C., in late summer 2001, for evaluation in spring 2002. The results from these trials demonstrated that NCS 93-05 had potential as a new cultivar. In 2001 NCS 93-05 was meristemmed in in-vitro culture at Raleigh, N.C., followed by virus testing, which determined that the meristemmed plants were free of known viruses. The meristemmed plants were also compared to original runner derived plants in field trials and were determined to be true to type phenotypically in both plant and fruit. Therefore the remaining trials, from 2004–2006, and all in the annual hill culture production system, were planted with runner plants derived from the virus tested meristem derived plants. These included replicated trials at Castle Hayne, Reidsville, and Fletcher, N.C., and Beltsville and Queenstown, Md. They also included grower trials at King's Mountain, Seven Springs, and Sanford, N.C., and Chambersburg, Pa. Based on performance in these replicated and grower trials it was determined that NCS 93-05 was worthy of release as a new strawberry cultivar for the southeastern USA. Plants and fruit of this new variety have remained true to type through successive cycles of asexual propagation by in-vitro multiplication following meristemming at Raleigh, N.C., and from runner plants from in-vivo plants in the field at Raleigh, Jackson Springs, Salisbury, and Laurel Springs, N.C. This new variety has been named the 'Galletta' cultivar.

SUMMARY OF THE INVENTION

'Galletta' is a new and distinct variety of strawberry plant that is broadly adapted across the southeastern USA. In most years, fruit yields have been equal to 'Camarosa' (U.S. Plant Pat. No. 8,708) and 'Chandler' (U.S. Plant Pat. No. 5,262), the standard cultivars currently grown in North Carolina, and also the recently cultivar 'Bish' (U.S. Plant Pat. No. 15,552). 'Galletta' fruit size was as large as or larger than fruit size of 'Camarosa', the largest fruited current standard cultivar grown in North Carolina. Average fruit attractiveness, symmetry, skin and flesh color, and flavor were equal or superior to the two standard cultivars and 'Bish'. Fruit firmness and skin toughness were also very good, though not quite as firm or tough as the extremely firm 'Camarosa'. 'Galletta' fruit ripened earlier than 'Bish', 'Camarosa', and especially 'Chandler'. It was consistently earlier than 'Bish' for date of first new leaf and flower and first ripe fruit. 'Galletta' plants were consistently less vigorous than 'Bish' as determined by leaf length (Galletta — 192 mm; Bish — 205 mm), leaf width (Galletta — 126 mm; Bish — 133 mm), leaflet length (Galletta — 63 mm; Bish — 72 mm), and leaflet width (Galletta — 51 mm; Bish — 62 mm). The orientation of pubescence on the leaf petioles of 'Galletta' was mostly perpendicular, and mostly basipetal on 'Bish'. The mid-tier leaflet shape of leaflets of 'Galletta' were broadly obovate while those of 'Bish' were elliptic to elliptic-obovate. The abaxial surface of the leaflets of 'Galletta' were lightly pubescent, and the abaxial surface of the leaflets of 'Bish' were glabrous. The diameter of both the outer and inner calyces of primary, secondary and tertiary flowers of 'Galletta' were consistently larger than those of 'Bish'. The number of sepals and petals on the primary and secondary flowers of 'Galletta' were also consistently higher than on 'Bish'. The flower petal shape on primary flowers of 'Galletta' were round to oval, while the shape of the petals on primary flowers of 'Bish' were obovate. The color of the anthers of 'Galletta' was yellow, and 'Bish' was yellow-orange. The flowers of 'Galletta' are self-fertile and produce abundant pollen. Primary berries of 'Galletta' were long-conic in shape while primary berries of 'Bish' were conic in shape. Skin color on the sun-exposed side of the berries of 'Galletta' was red (RHS 53A), while it was red-purple (RHS 59A) on 'Bish'. 'Galletta' usually avoids significant natural infection by anthracnose fruit rot in the field, in contrast to 'Camarosa' and 'Chandler', however it is not resistant to this disease.

BRIEF DESCRIPTION OF THE DRAWINGS

The photographs in the drawings were made using digital photography techniques, and illustrate the colors as true as reasonably possible when using these techniques. Colors in the photographs may differ slightly from the color values cited in the detailed botanical description, which accurately describe the colors of the new *Fragaria×ananassa* variety. All photographs were taken from plants growing in a cultivar trueness to type trial at Jackson Springs, N.C.

FIG. 1 shows the typical fruit shape and skin color of fruit of 'Galletta'.

FIG. 2 shows the typical fruit flesh color of 'Galletta'.

DETAILED BOTANICAL DESCRIPTION OF THE VARIETY

The following is a detailed botanical description of a new and distinct variety of *Fragaria×ananassa* Duchense plant known as 'Galletta'. The observations below are from mature plants grown in trueness to type test plots in annual hill culture on white/black plastic mulch with drip irrigation at Jackson Springs, N.C., in 2007. These test plots were established in fall 2006. For horticultural traits, the data were collected from mature plants grown in annual hill culture on black plastic mulch with drip irrigation at Castle Hayne, Reidsville and Fletcher, N.C. Those skilled in the art of cultivar description and evaluation will appreciate that certain characteristics of a variety will vary with older or younger plants. Also, 'Galletta' has not been observed under all possible environmental conditions. Where dimensions, sizes, colors and other characteristics are given, it is to be understood that such characteristics are approximations or averages set forth as accurately as practicable. The phenotype of the variety may differ from the descriptions herein with variations in the environment such as season, temperature, light intensity, day length and cultural conditions. Color notations are based on The Royal Horticultural Society Colour Chart, the Royal Horticultural Society, London, UK, 2001 edition.

For botanical description purposes, 'Galletta' was compared to 'Bish' for all morphological and ontogenetic traits because the two varieties are related and so it is important that they can be clearly differentiated. 'Earliglow' is one parent of 'Galletta' and a grandparent of 'Bish'. 'Galletta' was also compared to 'Chandler' and 'Camarosa', the two standard varieties currently grown commercially in North Carolina, for horticultural traits.

Plant:

*Canopy height.*—Galletta — 22.5 cm. Bish — 21.75 cm.

*Canopy density.*—Galletta — medium. Bish — medium.

*Crown diameter.*—Galletta — 9.5 mm. Bish — 9.7 mm

*Plant vigor.*—Galletta — medium. Bish — high.

*Date of first leaf.*—Galletta — March 6. Bish — March 8.

*Date of first flower.*—Galletta — March 6. Bish — March 10.

*Date of first ripe fruit.*—Galletta — April 7. Bish — April 11.

Leaves:

*Number of leaflets.*—Galletta — 3. Bish — 3.

*Mid-tier leaf length.*—Galletta — 192 mm. Bish — 205 mm.

*Mid-tier leaf width.*—Galletta — 126 mm. Bish — 133 mm,

*Leaf petiole length.*—Galletta — 134 mm. Bish — 131 mm,

*Leaf Petiole pubescence.*—Galletta — moderate. Bish — moderate.

*Orientation of leaf petiole pubescence.*—Galletta — mostly perpendicular to occasionally basipetal. Bish — mostly basipetal to occasionally perpendicular.

*Mid-tier leaf petiole bracts.*—Galletta — none. Bish — 1–2 occasionally and very small.

*Adaxial leaf surface color.*—Galletta — green (RHS 139A). Bish — green (RHS 137A).

*Abaxial leaf surface color.*—Galletta — yellow green (RHS 147B). Bish — yellow green (RHS 147B).

*Leaf petiole color.*—Galletta — yellow green (RHS 146D). Bish — yellow green (RHS 145B).

*Mid-tier leaflet length.*—Galletta — 63 mm. Bish — 72 mm.

*Mid-tier leaflet width.*—Galletta — 51 mm. Bish — 62 mm.

*Mid-tier leaflet length to width ratio.*—Galletta — 1.23. Bish — 1.16.

*Mid-tier center leaflet shape.*—Galletta — widely obovate. Bish — mostly elliptic to elliptic-obovate.

*Mid-tier lateral leaflet shape.*—Galletta — side adjacent to center leaflet obovate; side opposite center leaflet ovate. Bish — side adjacent to center leaflet quite variable, ovate to ovate elliptic to occasionally obovate; side opposite center leaflet ovate.

*Leaflet convexivity.*—Galletta — slightly concave to convex. Bish — slightly concave.

*Mid-tier leaflet serrations.*—Galletta — apical ⅔–¾ of the leaflet margin Bish — apical ⅔ of the leaflet margin.

*Mid-tier leaflet serration shape.*—Galletta — dentate and semipointed. Bish — dentate and blunt to semipointed.

*Adaxial leaflet surface pubescence.*—Galletta — light and only on the midvein. Bish — very sparse and only on the veins.

*Abaxial leaflet surface pubescence.*—Galletta — moderate on the veins and light on the blade. Bish — moderate on larger veins and sparse on branch veins, none on the leaf blade.

Flowers:

*Infloresence length.*—Galletta — same as canopy height (leaf length) — 192 mm. Bish — same as canopy height (leaf length) — 205 mm.

*Outer calx diameter.*—Primary flowers Galletta — 45 mm. Bish — 27 mm. Secondary flowers Galletta — 29 mm. Bish — 23 mm. Tertiary flowers Galletta — 26 mm. Bish — 18 mm.

*Inner calyx diameter.*—Primary flowers Galletta — 33 mm. Bish — 26 mm. Secondary flowers Galletta — 27 mm. Bish — 22 mm. Tertiary flowers Galletta — 24 mm. Bish — 19 mm.

*Sepal number.*—Primary flowers Galletta — 14 (7 each, outer and inner calyx). Bish — 11 (6 outer calyx, 5 inner calyx). Secondary flowers Galletta — 12 (6 each, outer and inner calyx). Bish — 10 (5 each, outer and inner calyx). Tertiary flowers Galletta — 10 (5 each, outer and inner calyx). Bish — 10 (5 each, outer and inner calyx).

*Sepal color.*—Adaxial surface of outer calyx Galletta — green (RHS 137B). Bish — green (RHS 137A). Abaxial surface of outer calyx Galletta — green (RHS 137C). Bish — green (RHS 138A). Adaxial surface of inner calyx Galletta — green (RHS N138B). Bish — green (RHS 138A). Abaxial surface of inner calyx Galletta — green (RHS 139C). Bish — green (RHS 138B at the base; RHS 139A at the tip).

*Corolla diameter.*—Primary flowers Galletta — 32 mm. Bish — 30 mm. Secondary flowers Galletta — 28 mm. Bish — 25 mm. Tertiary flowers Galletta — 27 mm. Bish — 24 mm.

*Number of flower petals.*—Primary flowers Galletta — 7. Bish — 5–6. Secondary flowers Galletta — 6. Bish — 5. Tertiary flowers Galletta — 5. Bish — 5.

*Flower petal length.*—Primary flowers Galletta — 12 mm. Bish — 12 mm. Secondary flowers Galletta — 11 mm. Bish — 10 mm. Tertiary flowers Galletta — 10 mm. Bish — 9 mm.

*Flower petal width.*—Primary flowers Galletta — 12 mm. Bish — 12 mm. Secondary flowers Galletta — 11 mm. Bish — 10 mm. Tertiary flowers Galletta — 10 mm. Bish — 8 mm.

*Flower petal length to width ratio.*—Galletta — 1.0 for primaries, secondaries, and tertiaries. Bish — 3 1.0 for primaries and secondaries; 1.1 for tertaries.

*Flower petal shape.*—Primary flowers Galletta — round to oval. Bish — obovate. Secondary flowers Galletta — round to round-ovate. Bish — obovate. Tertiary flowers Galletta — predominantly obovate, to occasionally round to round obovate. Bish — obovate.

*Flower petal color.*—Galletta — white (RHS 155C). Bish — white (RHS 155C).

*Anther color.*—Galletta — yellow (RHS 13A). Bish — yellow-orange (RHS 16A).

*Filament color.*—Galletta — yellow-green (RHS 149D). Bish — yellow-green (150C).

*Style color.*—Galletta — yellow-green (RHS 149D). Bish — yellow-green (RHS 150A).

*Stigma color.*—Galletta — yellow (RHS 2C). Bish — yellow (RHS 2D).

Fruit:

*Berry size.*—Primary berries Galletta — 32 g. Bish — 27 g. Secondary berries Galletta — 20 g. Bish — 16 g. Tertiary berries Galletta — 10 g. Bish — 7 g.

*Berry length.*—Primary berries Galletta — 51 mm. Bish — 45 mm. Secondary berries Galletta — 40 mm. Bish — 36 mm. Tertiary berries Galletta — 31 mm. Bish — 25 mm.

*Berry width.*—Primary berries Galletta — 36 mm. Bish — 36 mm. Secondary berries Galletta — 35 mm. Bish — 31 mm. Tertiary berries Galletta — 27 mm. Bish — 25 mm.

*Berry length to width ratio.*—Primary berries Galletta — 1.4. Bish — 1.2. Secondary berries Galletta — 1.1. Bish — 1.2. Tertiary berries Galletta — 1.1. Bish — 1.0.

*Berry shape.*—Primary berries Galletta — long conic (see FIG. 1). Bish — conic, with a blunt puckered tip. Secondary berries Galletta — conic. Bish — conic. Tertiary berries Galletta — conic. Bish — conic.

*Berry skin color.*—Exposed side Galletta — red (RHS 53A) (see FIG. 1). Bish — red purple (RHS 59A). Unexposed side Galletta — red (RHS 46A). Bish — red (RHS 46A).

*Berry skin glossiness.*—Galletta — uniformly glossy. Bish — subglossy.

*Berry interior color.*—Flesh color Galletta — orange red (RHS 34A) (see FIG. 2). Bish — orange red (RHS N34B). Berry core color Galletta — orange red (RHS 34B). Bish — orange red (RHS N34D).

*Berry calyx orientation.*—Galletta — clasped to somewhat reflexed, or occasionally reflexed (especially on tertiary berries). Bish — perpendicular to somewhat clasped.

Seeds:

*Seed position on the fleshy receptacle.*—Galletta — slightly indented to even with the berry surface. Bish — slightly indented.

*Seed shape.*—Galletta — oval. Bish — oval.

*Seed color.*—Galletta — mostly yellow green (RHS N144A), to sometimes orange red (RHS N34A) on the exposed side of the berries. Bish — red purple (RHS 59A) on the exposed side of the berries to mostly yellow green (RHS N144A) on the remaining surfaces.

The technical (pomological) descriptive data comparing 'Galletta' to 'Bish', 'Camarosa' and 'Chandler' at Castle Hayne, Fletcher and Reidsville, N.C., is presented in Tables 1–8.

Yield per plant: Total and especially marketable yield of Galletta was generally equal to (not significantly different from) or higher than the standard cultivars Camarosa and Chandler, and the recently released cultivar Bish (Tables 1–4), except for the later planting date for Castle Hayne in 2006 (Table 5). The data in Table 5 also suggests that Galletta may benefit from planting about seven days earlier than Camarosa and Chandler from the standpoint of yield.

TABLE 1

Yield, fruit size and fruit anthracnose infection of strawberry cultivars at Fletcher, NC, in 1999[1, 2].

| Cultivar | Total yield (g/plant) | Marketable yield (g/plant) | Fruit anthracnose[3] (% by weight) | Average fruit size (g/berry) |
|---|---|---|---|---|
| Bish | 674a | 580a | 1a | 15c |
| Camarosa | 638a | 445b | 30b | 18b |
| Chandler | 232b | 88c | 50c | 14d |
| Galletta | 604a | 546ab | 3a | 21a |

[1]Planted Aug. 17, 1998; 3 reps of 10 plants each.
[2]Numbers not followed by the same letter are significantly different at the 0.05 level (Duncan's Multiple Range Test).
[3]Natural infection by anthracnose fruit rot caused by *Colletotrichum acutatum*.

TABLE 2

Yield and fruit size of strawberry cultivars at Castle Hayne, NC, in 2004[1, 2].

| Cultivar | Total yield (g/plant) | Marketable yield (g/plant) | Average fruit size (g/berry) |
|---|---|---|---|
| Bish | 851b | 581 | 14.3c |
| Camarosa | 1333ab | 691 | 19.0ab |
| Chandler | 1607a | 974 | 17.0bc |
| Galletta | 1101ab | 664 | 22.9a |
| LSD 0.05 | 601 | ns | 4.3 |

[1]Planted Oct. 15, 2003; 3 reps of 10 plants each.
[2]Numbers not followed by the same letter are significantly different.

TABLE 3

Yield and fruit size of strawberry cultivars at Reidsville, NC. in 2005[1, 2].

| Cultivar | Total yield (g/plant) | Marketable yield (g/plant) | Average fruit size (g/berry) |
|---|---|---|---|
| Bish | 512ab | 422 | 16b |
| Chandler | 658a | 476 | 16b |
| Galletta | 427bc | 417 | 26a |
| LSD 0.05 | 182 | ns | 5 |

[1]Planted Sep. 15, 2004; 5 reps of 10 plants each.
[2]Numbers not followed by the same letter are significantly different.

TABLE 4

Yield, fruit size and ripening season of strawberry cultivars at Fletcher, NC, in 2005[1, 2].

| Cultivar | Total yield (g/plant) | Marketable yield (g/plant) | Average fruit size (g/berry) | Percent ripe through harvest five[3] |
|---|---|---|---|---|
| Bish | 494 | 400 | 12.6c | 28.5 |
| Chandler | 458 | 380 | 14.4b | 20.9 |
| Galletta | 467 | 325 | 18.2a | 50.4 |
| LSD 0.05 | ns | ns | 1.7 | |

[1]Planted Aug. 17, 2004; 5 reps of 10 plants each.
[2]Numbers not followed by the same letter are significantly different.
[3]Twice weekly harvests; first 2.5 weeks of the harvest season.

TABLE 5

Comparison of yield and size of strawberry cultivars across two planting dates at Castle Hayne, NC, in 2006[1, 2].

| Cultivar | Planting date | Total yield (g/plant) | Marketable yield (g/plant) | Average fruit size (g/berry) |
|---|---|---|---|---|
| Camarosa | Oct. 6, 2005[3] | 859 | 519 | 18.9 |
| | Oct. 13, 2005 | 816ab | 556ab | 21.2 |
| Chandler | Oct. 6, 2005 | 1005 | 637 | 16.9 |
| | Oct. 13, 2005 | 849a | 667a | 19.8 |
| Galletta | Oct. 6, 2005 | 871 | 660 | 20.0 |
| | Oct. 13, 2005 | 515b | 361b | 23.5 |
| LSD 0.05 | (Oct. 13, 2005) | 314 | 232 | ns |

[1]Three reps of 10 plants each on each planting date.
[2]Numbers not followed by the same letter are significantly different.
[3]No significant differences for the Oct. 6, 2005 planting date.

Average berry size: Average berry size (random across primary, secondary and tertiary ranks) of Galletta was consistently larger than Bish and Chandler, and equal to or larger than Camarosa in Tables 1–4. The same numerical size differences by planting date were also evident in Table 5, although the differences were not significant.

Pollination requirements: The flowers of Galletta are self-fertile.

Pollen production: Galletta flowers produce abundant pollen.

Ripening season: We typically determine the percent of fruit harvested through the first five harvests when harvesting twice weekly, or through the first two weeks when harvesting once weekly to ascertain differences in ripening season among cultivars. At Fletcher, N.C., in 2005 Galletta was 50% ripe after the first five harvests (twice weekly harvests), while Bish was 28% ripe and Chandler 21% ripe (Table 4). Camarosa was not included in this trial but it typically is very similar in ripening season to Bish.

Fruit anthracnose resistance: Anthracnose fruit rot caused by *Colletotrichum acutatum* is one of the most serious limiting factors to strawberry production in the southeastern US. In 1999 at Fletcher, N.C., a severe natural infection of this disease occurred in the experimental plot and gave a good indication of potential disease reaction among cultivars (Table 1). Both Bish and Galletta had very low incidences of anthracnose fruit rot under these conditions, while losses to this disease in Camarosa and Chandler were 30% and 50% respectively. In recent trials At Castle Hayne and Clinton, N.C., where plants were inoculated with C. acutatum in the field, both Bish and Galletta were determined to also be susceptible. So while Galletta does not have genetic resistance to anthracnose fruit rot, it typically avoids high levels of infection under natural conditions.

Fruit attractiveness: Fruit attractiveness refers to the overall appearance (eye appeal) and uniformity of the berries. Fruit attractiveness was determined using a subjective rating scale where less than 60 was unacceptable, 60–69 was acceptable, 70–79 was good, and 80 and above superior (Tables 6–8). Galletta was equal or superior to Bish, Camarosa, and Chandler for overall fruit attractiveness.

TABLE 6

Horticultural characteristics of the fruit of strawberry cultivars at Fletcher, NC, in 1999[1, 2].

| Cultivar | Attractiveness | Firmness | Fruit symmetry | Skin color | Flesh color | Skin toughness | Flavor |
|---|---|---|---|---|---|---|---|
| Bish | 76b | 80b | 76ab | 79ns | 71ns | 80b | 80a |
| Camarosa | 75b | 85a | 73bc | 78ns | 74ns | 84a | 68c |
| Chandler | 70c | 80b | 72c | 77ns | 75ns | 80b | 77b |
| Galletta | 80a | 80b | 78a | 80ns | 73ns | 80b | 78ab |

[1]Planted Aug. 17, 1998; 3 reps of 10 plants each; twice weekly harvest.
[2]Numbers not followed by the same letter are significantly different at the 0.05 level (Duncan's Multiple range Test).

TABLE 7

Horticultural characteristics of the fruit of strawberry cultivars at Castle Hayne, NC, in 2004[1, 2].

| Cultivar | Attractiveness | Firmness | Fruit symmetry | Skin color | Flesh color | Skin toughness | Flavor |
|---|---|---|---|---|---|---|---|
| Bish | 75.0a | 75.4b | 75 | 77.3a | 75.3b | 76.2b | 73.7a |
| Camarosa | 72.8b | 82.2a | 75 | 77.8a | 76.8ab | 81.1a | 70.0b |
| Chandler | 72.2b | 74.6b | 75 | 75.3b | 75.0b | 73.1c | 71.2b |
| Galletta | 74.9a | 74.9b | 76 | 78.2a | 77.6a | 76.1b | 73.6a |
| LSD 0.05 | 1.8 | 2.6 | ns | 1.9 | 2.1 | 2.8 | 2.0 |

[1]Planted Oct. 15, 2003; 3 reps of 10 plants each; once weekly harvest.
[2]Numbers not followed by the same letter were significantly different.

TABLE 8

Horticultural characteristics of the fruit of strawberry cultivars at Reidsville, NC, in 2005[1, 2].

| Cultivar | Attractiveness | Firmness | Fruit symmetry | Skin color | Flesh color | Skin toughness | Flavor |
|---|---|---|---|---|---|---|---|
| Bish | 77.3b | 79.4a | 77.8a | 78.2b | 69.8b | 78.4b | 75.1 |
| Chandler | 76.7b | 76.7b | 73.6b | 79.8a | 77.1a | 75.2c | 76.2 |
| Galletta | 80.3a | 81.0a | 79.5a | 80.0a | 77.6a | 80.5a | 75.0 |
| LSD 0.05 | 1.9 | 1.8 | 2.8 | 1.2 | 1.7 | 1.5 | ns |

[1]Planted Sep. 15, 2004; 5 reps of 10 plants each; once weekly harvest.
[2]Numbers not followed by the same letter were significantly different.

Fruit firmness: Fruit firmness is largely a measure of the firmness of the flesh as regards resistance to bruising and softening. It is a very important trait from the standpoint of post harvest shelf life of the berries (i. e. firmer berries usually have longer shelf life). This trait was determined subjectively by gently pressing individual berries between the thumb and forefinger and assigning each berry a numerical score where less than 60 was unacceptable, 60–69 was acceptable, 70–79 was average to good, and 80 and above superior. Galletta was equal to Bish and Chandler, but not as firm as Camarosa in Tables 6 and 7 at Fletcher and Castle Hayne, N.C., respectively. Fruit firmness of Galletta was superior to Chandler and equal to Bish at Reidsville, N.C. (Table 8). Overall, Galletta was rated superior for fruit firmness at Fletcher and Reidsville, and good at Castle Hayne.

Fruit symmetry: Fruit symmetry refers to uniformity of shape and smoothness and freedom from irregularities in the skin of the berry. Fruit symmetry was determined subjectively where less than 60 was unacceptable, 60–69 was acceptable, 70–79 was average to good, and 80 and above superior. Galletta was equal to Bish and superior to Camarosa and Chandler for fruit symmetry at Fletcher, N.C. (Table 6). It was also equal to Bish and superior to Chandler at Reidsville, N.C., for fruit symmetry (Table 8). There were no significant differences among cultivars for fruit symmetry at Castle Hayne, N.C. (Table 7).

Skin color: Skin color was also rated subjectively in replicated yield plots where less than 60 was unacceptable, 60–69 was acceptable (pale red; or very dark red), 70–79 was average to good (light to medium red), and 80 and above superior (dark red). Galletta was equal to Bish and Camarosa and superior to Chandler for skin color at Castle Hayne, N.C. (Table 7). It was equal to Chandler and superior to Bish for skin color at Reidsville, N.C. (Table 8). There were no significant differences among cultivars for skin color at Fletcher, N.C. (Table 6).

Flesh color: Fruit flesh color was determined subjectively with less than 60 being unacceptable (white), 60–69 acceptable (pale red), 70–79 average to good (light red to medium red), and 80 and above superior (dark red). Galletta was equal to Camarosa and superior to Bish and Chandler for flesh color at Castle Hayne, N.C. (Table 7). It was equal to Chandler and superior to Bish at Reidsville, N.C. (Table 8). There were no differences among cultivars for flesh color at Fletcher, N.C. (Table 6).

Skin toughness: Skin toughness refers to the resistance of the skin to abrasion. Cultivars with tender skins prone to abrasion tend to leak juice which leads to an unattractive package and fungal attacks which render the fruit unsalable. Skin toughness was evaluated subjectively where less than 60 was unacceptable (very tender skin), 60–69 was acceptable (somewhat tender skin), 70–79 was average to good (moderately tough skin only occasionally subject to abrasion), and 80 and above, superior (tough skin not subject to abrasion). Galletta was equal to Bish and Chandler for skin toughness at Fletcher, N.C., but not as good as Camarosa (Table 6). At Castle Hayne, N.C., Galletta skin toughness was superior to Chandler and equal to Bish, but again it was not equal to Camarosa (Table 7). At Reidsville, N.C., Galletta was superior to both Bish and Chandler for skin toughness (Table 8). Even though the skin of fruit of Galletta was not as tough as Camarosa, it rated superior for this trait in two of the three trials which is quite good.

Flavor: Fruit flavor was evaluated subjectively with less than 60 being unacceptable (totally lacking in flavor; or with an unacceptable off-flavor), 60–69 was acceptable (relatively bland, but acceptable), 70–79 was average to good (reasonably good combination of sweetness, acidity and aroma), and 80 and above superior (outstanding combination of sweetness, acidity and characteristic strawberry aroma). Galletta was equal to Bish and superior to Camarosa and Chandler for flavor at Fletcher and Castle Hayne, N.C. (Tables 6 and 7). There were no differences among cultivars for flavor at Reidsville, N.C. (Table 8).

That which is claimed is:

1. A new and distinct variety of commercial strawberry plant (*Fragaria×ananassa* Duchense) substantially as illustrated and described, characterized by its early season ripening, large fruit size, high yields, very attractive symmetrical good quality fruit with good flesh firmness and skin toughness, deep red skin color and medium red flesh color, and broad adaptation across the southeastern US.

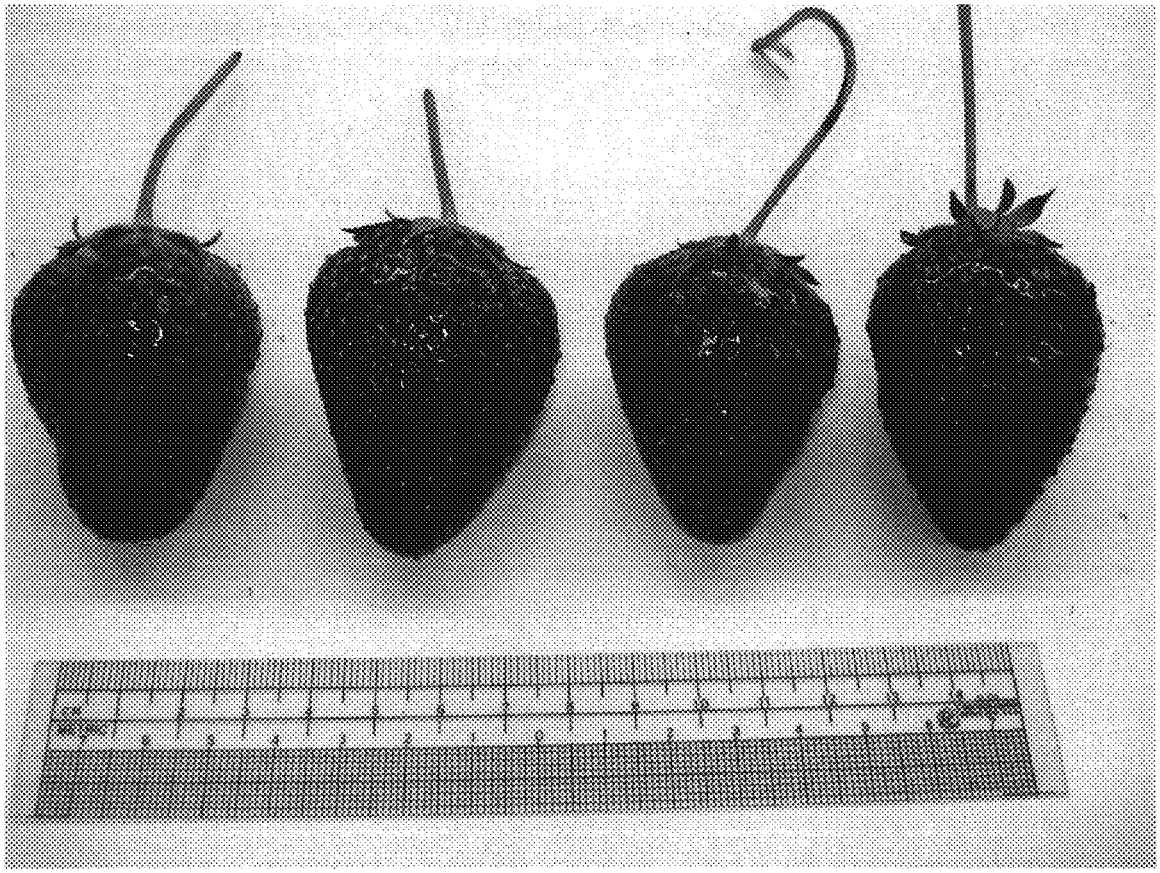

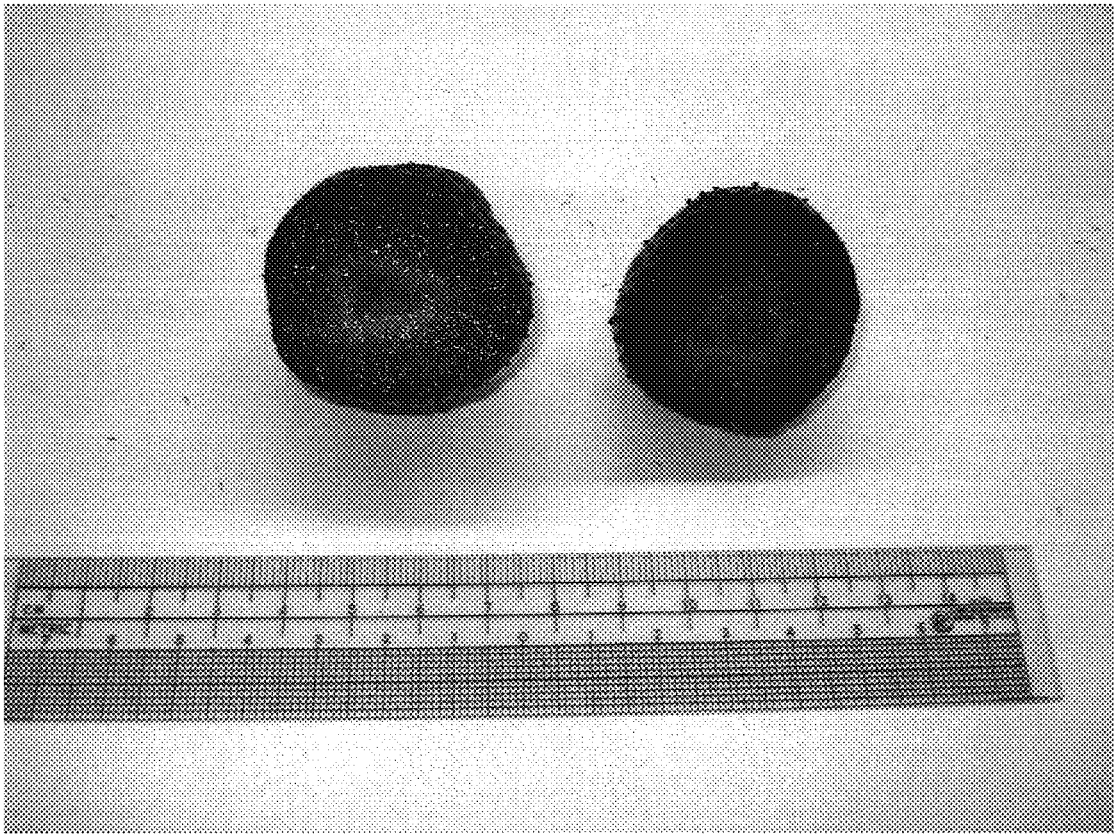

* * * * *